United States Patent [19]

Meilland

[11] Plant 5,180

[45] Jan. 24, 1984

[54] MINIATURE ROSE PLANT—MEIFINARO VARIETY

[75] Inventor: Marie L. Meilland, Antibes, France

[73] Assignee: The Conard-Pyle Company, West Grove, Pa.

[21] Appl. No.: 392,257

[22] Filed: Jun. 25, 1982

[30] Foreign Application Priority Data

Jul. 1, 1981 [FR] France ..... 3132

[51] Int. Cl.[3] ..... A01H 5/00

[52] U.S. Cl. ..... Plt./9

[58] Field of Search ..... Plt./9

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided having attractive well formed very double blossoms which are neyron pink in coloration. The new variety resulted from the crossing of Meirotego variety with pollen from an unnamed seedling which was formed by crossing the Meilucca and Perla de Montserrat varieties. The new variety has a compact and vigorous growth habit and is well adapted for landscape uses.

21 Drawing Figures

SUMMARY OF THE INVENTION

The new and distinct variety of rose plant of the Miniature Class was originated by me by crossing the Meirotego variety (non-patented) with pollen from an unnamed and non-patented variety formed by crossing the Meilucca variety (non-patented) and the Perla de Montserrat variety (non-patented). The parentage of the new variety can be summarized as follows:

Meirotego × [Meilucca × Perla de Montserrat].

From this controlled pollination I produced a new and distinct variety of rose plant of the Miniature Class which is distinguished from its parents, as well as from all other varieties of which I am aware. This variety was obtained through the selective study of a large number of distinct plants which resulted from the above cross. A single plant resulting from this cross possessed the characteristics of the presently claimed variety.

It was found that the new variety as illustrated herein possesses (a) a compact and vigorous growth habit, (b) bronzed green adult wood, and (c) the abundant and continuous formation of attractive well formed very double blossoms which are neyron pink in coloration.

The new variety additionally matures quickly, and forces well. Its propensity to continuously produce well formed beautiful neyron pink blossoms (as described) in profusion is impressive. The blossoms have a long life and the petals tend to drop off cleanly. The new variety is not particularly susceptible to cryptogamic diseases.

Extensive testing has confirmed the behavior and characteristics of the new variety. The new variety is particularly suited for growing in parks and gardens.

The characteristics and properties of the new variety are strictly transmissible by asexual propagation, e.g. by budding.

The rose plant of the new variety has been designated the Meifinaro variety.

BRIEF DESCRIPTION OF THE PHOTOGRAPH

The accompanying photograph shows as nearly true as it is reasonably possible to make the same in a color illustration of this character, typical specimens of plant parts of the new variety observed during August and cultivated in a greenhouse at Le Cannet des Maures, Var, France. The rose plants of the new variety were two years of age and were grafted on *Rosa indica.*

FIG. 1—illustrates a specimen of a young shoot;

FIG. 2—illustrates a specimen of a young shoot with three buds before the opening of the sepals;

FIG. 3—illustrates a specimen of a young shoot wherein the sepals have begun to open on the center bud, and the sepals have not yet begun to open on the outside buds;

FIG. 4—illustrates a specimen of a bud as the petals begin to open;

FIG. 5—illustrates a specimen of a flower in the course of opening;

FIG. 6—illustrates a specimen of a flower in the course of opening at a later stage than shown in FIG. 5;

FIG. 7—illustrates a specimen of a fully opened flower—plan view—obverse;

FIG. 8—illustrates a specimen of a fully opened flower—plan view—reverse;

FIG. 9—illustrates a specimen of a flower at the end of the blooming stage—plan view—obverse;

FIG. 10—illustrates a specimen of a flower at the end of the blooming stage—plan view—reverse;

FIG. 11—illustrates a specimen of a floral receptacle showing the arrangement of the stamens (sepals and petals removed);

FIG. 12—illustrates a specimen of a floral receptacle showing the arrangement of the pistils (sepals, petals, and stamens removed);

FIG. 13—illustrates a specimen of a petal—obverse;

FIG. 14—illustrates a specimen of a petal—reverse;

FIG. 15—illustrates a specimen of a young flowering stem;

FIG. 16—illustrates a specimen of a main branch;

FIG. 17—illustrates a specimen of a leaf with three leaflets—upper surface;

FIG. 18—illustrates a specimen of a leaf with five leaflets—upper surface;

FIG. 19—illustrates a specimen of a leaf with seven leaflets—under surface;

FIG. 20—illustrates a specimen of a leaf with nine leaflets—upper surface; and FIG. 21—illustrates several leaf specimens wherein small supplementary leaflets additionally are present.

DETAILED DESCRIPTION

Figures 1, 2, 3, 4, 5, 6, 7, 8, 9, 10, 11, 12, 13, 14, 15, 16, 17, 18, 19, 20, 21:
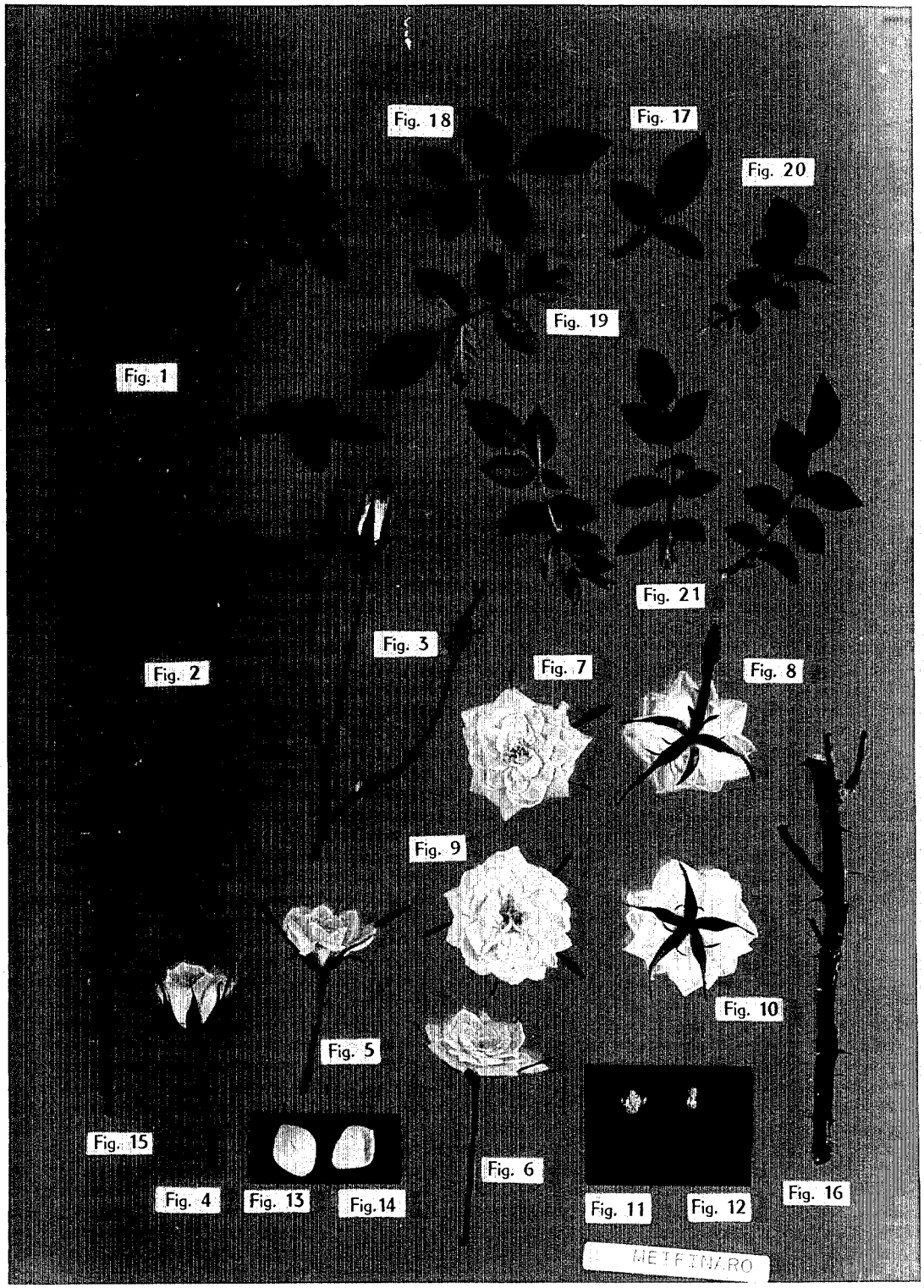

The plants described were grown in pots in greenhouses at Le Cannet des Maures, Var, France.

The chart used in the identification of the colors is that of The Royal Horticultural Society (R.H.S. Colour Chart). The terminology preceding the numbered references has been added to designate in common terms, the corresponding colors.

Class: Miniature.

Plant:

*Height.*—45 cm. on average.

*Breadth.*—45 cm. on average.

*Habit.*—Compact and bushy.

Branches:

*Color.*—Young stems: bronzed green, Yellow-Green Group 146A. Mature wood: slightly darker bronzed green, Yellow-Green Group 146A.

*Thorns.*—Shape. Upper edge: straight, very tapered, and slightly curved downwards. Under edge: slightly concave. Size: small. Quantity: fairly numerous. Color: On young stems: greenish. On mature wood: straw then becoming havana brown.

Leaves:

*Stipules.*—Adnate, pectinate, rather narrow.

*Petioles.*—Inner surface: grooved, medium green, edged with reddish brown on very young foliage, edges are more or less glandular. Outer surface: light green. This side carries a few small hooked thorns.

*Leaflets.*—Number: 3-5-7 (most frequently) and sometimes 9. Small leaflets are sometimes additionally present as illustrated in FIG. 21. Shape: oval with cuneiform base. Serration: simple and regular. Texture: leathery. General effect: small, rather dense, dull colored. Color: young foliage: Upper surface: dark green, Yellow-Green Group 147A, more or less spotted with reddish brown on very young foliage. Under surface: light green, Yellow-Green Group 147C, more or less spotted reddish brown on very young foliage. Color: adult foliage: Upper surface: dark green, Yellow-Green Group 147A. Under surface: light green, Yellow-Green Group 147C.

Inflorescence:

*Number of leaves.*—Usually 1 to 5 per stem.

*Peduncle.*—Straight, rigid, light green, smooth. It bears no glands, hair, or thorns. Length: approximately 4.5 to 5.5 cm.

*Sepals.*—Upper surface: tomentous, greenish. Under surface: light green. The outside sepals have slightly glandular and slightly appendiculate edges.

*Buds.*—Shape: oval before the opening of the sepals. Length: 1.3 cm. on average, not counting the calyx, at the opening of the sepals. Size: rather small. Color: when opening: both surfaces light mimosa yellow, Yellow Group 8C, more or less suffused with a large neyron pink edge, Red Group 55B.

*Flower.*—Form: very double and well formed. Shape: at first a hollow cup, later a flattened cup. Diameter: 3.7 cm. on average. Color: when opening fully: both surfaces light mimosa yellow, Yellow Group 8C, more or less suffused with a large edge of neyron pink, Red Group 55B. Color: during final bloom stage: both surfaces light mimosa yellow, Yellow Group 8D, slightly suffused with a large edge of neyron pink, Red Group 55B. When the petals drop the flower has changed to a nearly completely white coloration. Fragrance: none. Lasting quality: long. Corolla: petals: Texture: consistent. Form: ovoid with small point at the tip. The outside petals are rather large and inside petals are small and narrow. The unguis is small and mimosa yellow, Yellow Group 8B, on both faces. Number: 50 on average. Stripping: The petals fall cleanly after the normal life of the bloom has ended. Stamens: number: 37 on average. Anthers: yellow and edged with ocher. Filaments: yellow and irregular in height. Pistils: number: 28 on average. Stigmas: straw colored. Styles: more or less twisted, greenish in coloration with a fuschia tip. Receptacle: light green, at the dehiscence of the anthers and in longitudinal cross-section it is very narrow and funnel shaped.

Development:

*Vegetation.*—Vigorous.

*Blossoming.*—Abundant and nearly continuous.

*Resistance to diseases.*—Very good.

I claim:

1. A new and distinct variety of Miniature rose plant, substantially as herein shown and described, characterized particularly by (a) a compact and vigorous growth habit, (b) bronzed green adult wood, and (c) the abundant and continuous formation of attractive well formed very double blossoms which are neyron pink in coloration.

* * * * *

METFINARO